United States Patent [19]

Teeple

[11] Patent Number: 4,616,641

[45] Date of Patent: Oct. 14, 1986

[54] SURGICAL SHIELD

[76] Inventor: Edward Teeple, 641 Ridgefield Ave., Pittsburgh, Pa. 15216

[21] Appl. No.: 695,471

[22] Filed: Jan. 28, 1985

[51] Int. Cl.⁴ .............................................. A61F 13/00
[52] U.S. Cl. .............................. 128/132 R; 128/303.1
[58] Field of Search ............ 128/132 R, 132 D, 303.1

[56] References Cited

U.S. PATENT DOCUMENTS

| 4,024,862 | 5/1977 | Collins | 128/132 D |
| 4,450,845 | 5/1984 | Engel | 128/132 R |
| 4,520,814 | 6/1985 | Weeks | 128/303.1 |

FOREIGN PATENT DOCUMENTS 2207387  8/1973  Fed. Rep. of Germany ... 128/303.1

Primary Examiner—Dalton L. Truluck
Attorney, Agent, or Firm—Reed Smith Shaw & McClay

[57] ABSTRACT

A surgical shield for use during surgical procedures in which lasers are utilized and which comprises a fabric inner sheet interpositioned between a pair of coextensive metal foil sheets. The three sheets are attached together at their peripheries.

6 Claims, 3 Drawing Figures

SURGICAL SHIELD

FIELD OF THE INVENTION

The present invention relates to a surgical shield or blanket, and, in particular, to an aluminized blanket useful in protecting patients during surgical procedures involving lasers and in protecting anesthesia circuits from exposure to laser radiation.

BACKGROUND OF THE INVENTION

It is becoming more common to use lasers to perform various surgical techniques. As is well known, the radiation from such lasers must be confined to the operative area, however, it is equally well known that it is difficult, if not impossible, to prevent the occurrence of stray radiation in the operating rooms. Operating room personnel have begun wearing protective eye glasses and patients undergoing such procedures have been provided moistened guaze over the eyes, More recently, a surgical eye mask has been developed to protect the patient's eyes during laser surgery, see U.S. patent application Ser. No. 661,120.

The need for better protection for both the patient and the operating personnel during laser surgery has become apparent. The patient may be injured by direct exposure to the beam on the skin causing burns or flesh wounds or opthalmic injury or loss of vision if the eyes were to become accidentally exposed. The patient is highly at risk during the anesthesia, if such is a general anesthesia, since the patient is unable to alert the surgical personnel of the occurrence of an injury. The current use of wet towels is not a satisfactory method, because the sterile plastic sheet below the towel can be ignited by the laser beam, bacterial contamination occurs when plastic sheets are not used, and a potential of fire from towels which have not been remoistened during the operative procedure.

The problems encountered by patients are also encountered by the operating room personnel, but to a much lesser extent. The operating room personnel to some extent can avoid continued contact from the beam by stepping out of its path or alerting the user. Nevertheless, it is not always possible to remove oneself from the path of the beam and even short exposures may cause injury.

Another problem encountered is the exposure of the anesthesia machine and circuits to the laser radiation. The anesthesia circuit often lies near the operative field, especially during neurosurgery or during ENT surgery. Typically, these circuits have been wrapped in aluminum foil to deflect the stray radiation. However, such wrapping prevents the anesthesiologist from observing these circuits. Further, aluminum foil is very difficult to work with, especially around the endotracheal tube.

Accordingly it is an object of the present invention to provide a surgical shield to protect patients, operating room personnel, and anesthesia circuit/machines during laser surgery. It is a further object of the invention to provide a shield for anesthesia circuit which provides a snug fit over the circuit but also affords the anesthesiologist a view of the circuits during the operation.

SUMMARY OF THE INVENTION

Generally, the present invention provides a blanket or shield which is comprised of at least one first and at least one second outer metalic sheets, preferably of an aluminum foil, which have sandwiched therebetween gauze. The outer periphery of the first and second sheets is fastened together to interpose therebetween the gauze and to form the blanket. Eyelets are preferably positioned along an edge or outer portion of the periphery so that it can be hung in the operating room to partially isolate the laser beam from the operating room personnel.

In another embodiment of the invention, the blanket is provided with concentric precut or perforated openings to afford the surgeon access to the operative field. Any configuration or design of perforation can be used, but concentric circles or ellipses are most desirable for the typical laser operation. In this embodiment it is desirable to provide an adhesive coating on one side of the blanket to prevent movement on the patient's body.

For use in protecting an anesthesia circuit, the above described shields can be utilized. However, it is more desirable to form the blanket or shield with an elastic material at the distal and proximal sides to allow the shield to snugly fit over the circuit. Additionally, it is desirable to wrap the shield over the circuit in a "c"-configuration and to provide either fixed or removable straps to provide a view to the circuits. These and other advantages of the present invention will become apparent from a perusal of the following detailed description of the presently preferred embodiments of the invention taken in connection with the accompanying drawings.

PRESENTLY PREFERRED EMBODIMENTS

Figure 1:
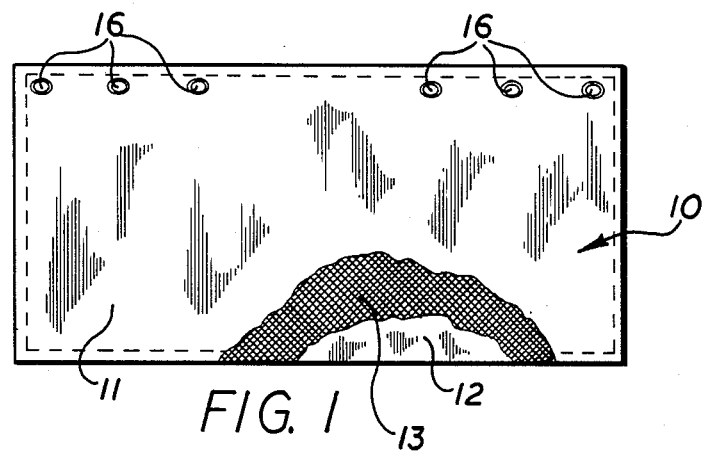
FIG. 1 is an elevation of the shield the present invention, shown in partial break away, for patient or operating room personnel use during laser surgery.

Referring to FIG. 1, laser shield 10 of the present invention is shown. Laser shield 10 comprises first and second metallized sheets 11 and 12, respectively. Interposed between first and second sheets 11 and 12 is inner fabric 13, Fabric 13 is preferably a cotton gauze but may be any sterilizable, pliable fabric. Outer sheets 11 and 12 are preferably formed from aluminum foil having a thickness of approximately 3 mils. The thickness of the foil is not critical, but it is to be understood that if the foil is too thin it is subject to being easily damaged during use, on the other hand, the foil is exceptionally heavy, it become unwieldy and unmanageable on the operating table or patient. Also, the foil may have a matte finish or surface. Many applications having a matte finish may be preferable for beam dispersion.

Shield 10 can be used to cover the patient to protect the patient from laser radiation during surgery as well as over the anesthesia circuits. In addition to use by patients, the shield can be used by operating room anesthesia personnel. In the latter case it is desirable to include eyelets 16 along portions of the periphery of the shield 10. Use of eyelets 16 permits shield 10 to be strategically placed in the operating room to isolate the laser and its beam from the operating room anesthesia personnel. It can be appreciated that other forms of fasteners or hangers can achieve the same purpose.

Figure 3:
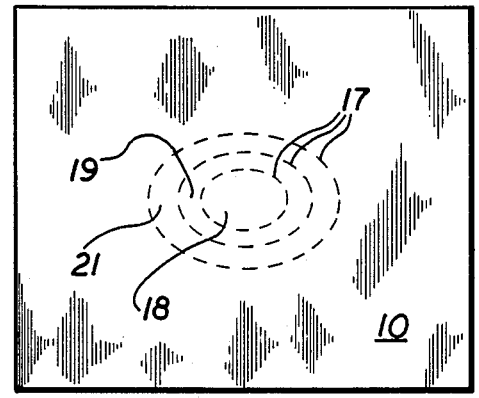
FIG. 3 is a elevation of the blanket for patient use and show precut operative opening or perforations.

Another feature of shield 10 is shown in FIG. 3, in which precut perforations 17 are provided. Preferably, perforations are concentrically arranged circles or ellipses which the surgeon can remove to expose an operating field on the patient's body. Removing the innermost area 18 to the outermost area 21 exposes an increasingly larger field in which to operate. Where the shield is to be used to protect a patient during laser surgery, it is desirable to include on the side facing the patient an adhesive to prevent movement of shield during the operative procedure. Further, in such surgical procedures, it is preferable to utilize only one sheet of foil rather than the multiply shield described above.

Figure 2:
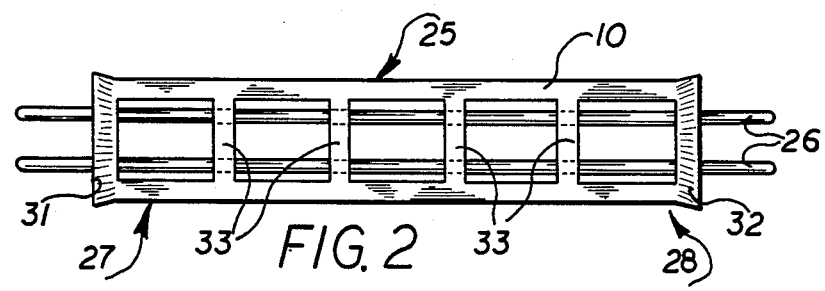
FIG. 2 is a side elevation of the present invention and for shield anesthesia circuits.

With reference to FIG. 2, shield 10 is formed in a sheath configuration 25 for protection of anesthesia circuits 26. Preferably sheath 25 includes at its distal and proximal sides 27 and 28, respectively, elastic sleeves 31 and 32. Elastic sleeves 31 and 32 permit sheath 25 to engage circuits 26 and also permit sliding movement along the length of the circuits. In the preferred embodiment, straps 33 are provided to attach the peripherial edges of shield 10 together. By use of such straps or other spaced fastening means 33, the circuits 26 remain in full view of the anesthesiologist during the operation.

While presently preferred embodiments of the invention have been shown and described in particularity, it may be otherwise embodied within the scope of the appended claims.

I claim:

1. A surgical shield for use during laser procedures comprising:

a. a fabric inner sheet
   b. first metallic foil sheets respectively positioned over each side of said fabric inner sheet to coextensively interpose said fabric sheet between said foil sheets; and
   c. means for attaching together the respective foil and fabric sheets about their peripheries, and further wherein said foil sheets and fabric sheet includes at least one bounded perforation for removing the area bounded thereby to expose an operative field.

2. A surgical shield as set forth in claim 1, wherein said periphery includes a plurality of eyelets to support said shield.

3. A surgical shield as set forth in claim 1, wherein opposing edges include elastic material and said shield is folded to provide a "c"-shape, and including means attached to the edge of an outer sheet spanning the open porion of the "c", whereby an indwelling anesthesia circuit is insulated from stray laser radiation.

4. A surgical shield as set forth in claim 1, wherein said foil is aluminum and said fabric inner sheet comprises cotton fabric.

5. A surgical shield as set forth in claim 1, wherein said foil is aluminum and said fabric inner sheet comprises cotton gauze.

6. A surgical shield as set forth in claim 1, wherein at least one of said foil sheets has an outer matte surface finish.

* * * * *